US009535014B1

(12) United States Patent
Feldman et al.

(10) Patent No.: US 9,535,014 B1
(45) Date of Patent: Jan. 3, 2017

(54) SYSTEMS AND METHODS FOR INSPECTING AN OBJECT

(71) Applicant: Applied Materials Israel, Ltd., Rehovot (IL)

(72) Inventors: Haim Feldman, Nof-Ayalon (IL); Ido Dolev, Rehovot (IL); Ido Almog, Rehovot (IL)

(73) Assignee: Applied Materials Israel Ltd., Rehovot (IL)

( * ) Notice: Subject to any disclaimer, the term of this patent is extended or adjusted under 35 U.S.C. 154(b) by 0 days.

(21) Appl. No.: 14/800,625

(22) Filed: Jul. 15, 2015

(51) Int. Cl.
*G01N 21/00* (2006.01)
*G01N 21/95* (2006.01)
*G02B 26/12* (2006.01)

(52) U.S. Cl.
CPC ......... *G01N 21/9501* (2013.01); *G02B 26/123* (2013.01); *G02B 26/124* (2013.01)

(58) Field of Classification Search
CPC ...... G01N 21/00; G02B 26/123; G02B 26/124
USPC ...................................... 356/237.2
See application file for complete search history.

(56) References Cited

U.S. PATENT DOCUMENTS

| 7,053,395 | B2 * | 5/2006 | Feldman | G01N 21/8806 250/208.1 |
| 2012/0086937 | A1 * | 4/2012 | Feldman | G01N 21/8806 356/237.2 |

* cited by examiner

*Primary Examiner* — Roy M Punnoose
(74) *Attorney, Agent, or Firm* — Kilpatrick Townsend & Stockton LLP

(57) ABSTRACT

A system, including an illumination module that comprises (a) a first traveling lens acousto-optic device; (b) a light source for illuminating the first traveling lens to provide an input beam that propagates along a first direction; (c) illumination optics for outputting an output beam that scans the object at a second direction; a detection unit; and a collection module for collecting a collected beam from the object, wherein the collected beam propagates along a third direction; and optically manipulating the collected beam to provide a counter-scan beam is directed towards the detection unit and has a focal point that is positioned at a same location regardless of the propagation of the collected beam along the third direction.

15 Claims, 9 Drawing Sheets

Directing, by a beam splitter, the collected beam to provide a third intermediate beam that impinges on a rotating polygon mirror. While the third intermediate rotates along a first rotation direction the rotating polygon mirror rotates at a same rotational rate but along an opposite rotation direction thereby countering the rotation of the third intermediate beam. 256

↓

Reflecting, by facets of the rotating polygon mirror, the third intermediate beam to provide a rotating polygon mirror output beam that is static when reflected by the facets of rotating polygon mirror. 257

↓

Outputting from the second scan lens the counter-scan beam. 258

SYSTEMS AND METHODS FOR INSPECTING AN OBJECT

BACKGROUND OF THE INVENTION

A variety of systems are used for automated inspection of semiconductor wafers, in order to detect defects, particles and/or patterns on the wafer surface as part of a quality assurance process in semiconductor manufacturing processes. It is a goal of current inspection systems to have high resolution and high contrast imaging in order to provide the reliability and accuracy demanded in sub-micron semiconductor manufacturing processes. However, it is also important to have a high-speed process that permits a large volume throughput so that the quality and assurance processes do not become a bottleneck in the wafer production process. Accordingly, the optical inspection systems must use shorter wave lengths, higher numerical aperture optics and high density image capture technology in order to enable the processing of data from such systems at sufficiently high rates that will satisfy the desired product throughput requirements.

A conventional imaging architecture that is used in wafer inspection systems at this time utilizes multi spot scanning laser for high-speed imaging. However, the data rates achievable by such architectures are limited by the physical constraints that arise due to limitations in the speed and quality of the single laser beam, the applicable optical system and related detection devices. For example, the single laser acting as a point light source is focused as a spot onto the object under inspection and is scanned across the surface of the object, which may be stationary or moved on a stage mechanism in coordination with the scan. The reflected light from the object is then imaged onto a detector, which generates pixel data from the scanning process.

The detector may be a photo multiplier detector (PMT) or a CCD array, whose individual elements are positioned to receive the reflected light as the beam is scanned and be read our serially, in a conventional fashion. While a high resolution may be obtained from such point source illumination, the requirement to scan each point in the field in order to construct a viewable image subjects the system to a limitation on its throughput.

The detector has to image the entire scan path of the spot and may collect stray light or other noises. The scanning of the single laser beam may be accomplished by a rotating mirror system, as seen in U.S. Pat. No. 5,065,008 or an acousto-optic cell. However, these single spot scanning architecture necessarily have a limited speed and are possibly subject to scan aberrations, low illumination brightness and potential thermal damage to the object when high brightness laser sources are used. The high data rates required to inspect the submicron structures of current semiconductor products cannot be achieved, even when a stage-type scanning system is used that moves the object relative to a fixed illumination and image location while a synchronized scanning pattern is produced by moving the single point of light over an area at the fixed location.

One way to increase the throughput of the inspection is to scan the object with a rectangular grid of beams, wherein the scan axis is parallel to the columns of the grid.

When the object is scanned with multiple beams the detector may also suffer from cross talk between the multiple beams.

Accordingly, there is a need for an object scanning system that will improve object throughput, while maintaining or even improving the reliability and accuracy of the data collected during the scan of an object, whether in a stationary or stage-type system.

SUMMARY

According to an embodiment of the invention there may be provided a system for inspecting an object, the system may include an illumination module that may include (a) a first traveling lens acousto-optic device that may be configured to generate a first traveling lens that propagates through an active region of the first traveling lens acousto-optic device; (b) a light source that that may be configured to illuminate the first traveling lens to provide an input beam that propagates along a first direction; (c) illumination optics that may be configured to receive the input beam and to output, in response to the input beam, an output beam that scans the object at a second direction; a detection unit; and a collection module that may be configured to (a) collect a collected beam from the object, the collected beam propagates along a third direction; and (b) optically manipulate the collected beam to provide a counter-scan beam is directed towards the detection unit and has a focal point that is positioned at a same location regardless of the propagation of the collected beam along the third direction.

The collection module may be configured to counter-scan the collected beam to provide the output beam.

The collection module may include a second traveling lens acousto-optic device that may be configured to generate a second traveling lens that propagates through an active region of the second traveling lens acousto-optic device along a fourth direction.

The illumination module may include a first scan lens and the collection module may include a mirror, and a second scan lens and an aperture; and the mirror, the second scan lens and the aperture are positioned between the second traveling lens acousto-optic device and the detection unit.

The traveling lens may propagate through the active region in synchronization with the propagation of the collected beam along the third direction.

An output beam of the second traveling lens acousto-optic device may impinge on the mirror and may be directed by the mirror towards the second scan lens to provide a mirror output beam that propagates along a fifth direction while maintaining a fixed angle in relation to the second scan lens; and the second scan lens may be configured to receive the mirror output beam to provide the counter-scan beam.

The illumination module may include a telescope lens, a beam splitter and an objective lens; the collection module may include the beam splitter, the objective lens and a tube lens; the telescope lens is positioned between the beam splitter and the first scan lens; and the tube lens is positioned between the beam splitter and the second traveling lens acousto-optic device.

The collection module may optically manipulates the collected beam to provide an intermediate beam that rotates counterclockwise; and the collection module may include detection unit optics and a rotating polygon mirror that may be configured to rotate in a clockwise direction in synchronicity with the counterclockwise rotation of the intermediate beam and to reflect, during multiple points in time, and towards the detection unit optics the output beam.

The illumination module may include a first scan lens, a telescope lens, a beam splitter and an objective lens; the collection module may include the beam splitter, the objective lens, a second scan lens and an aperture; and the beam splitter directs the intermediate beam towards the rotating polygon mirror.

The collection module may optically manipulate the collected beam to provide an intermediate beam that rotates counterclockwise; and the collection module may include detection unit optics and a rotating polygon mirror that may be configured to rotate in a clockwise direction in synchronicity with the counterclockwise rotation of the intermediate beam and to reflect, during multiple points in time, and towards the detection unit optics the output beam.

The illumination module may include a first scan lens, a telescope lens, a beam splitter and an objective lens; the collection module may include the beam splitter, the objective lens, a second scan lens and an aperture; and the beam splitter directs the intermediate beam towards the rotating polygon mirror.

The traveling lens acousto-optic device may be configured to generate a set of first traveling lenses that propagates through the active region of the first traveling lens acousto-optic device; the light source may be configured to illuminate the set of first traveling lenses to provide a set of input beams that propagates along the first direction; the illumination optics may be configured to receive the set of input beams and to output, in response to the set of input beams, a set of output beams that scans the object along the second direction; the collection module may be configured to (a) collect a set of collected beam from the object, the set of collected beam propagates along a third direction; and (b) optically manipulate the collected beam to provide a set of counter-scan beams that is directed towards the detection unit; and each counter-scan beam of the set of counter-scan beams has a focal point that is positioned at a same location regardless of the propagation of the set of collected beams along the third direction.

The collection module may include a second traveling lens acousto-optic device that may be configured to generate a set of second traveling lenses that propagates through the active region of the second traveling lens acousto-optic device along the fourth direction.

The illumination module may include a first scan lens and the collection module may include a mirror, a set of second scan lenses and a set of apertures, the mirror, the set of second scan lenses and the set of apertures are positioned between the second traveling lens acousto-optic device and the detection unit; the detection unit may include a set of detectors; and each detector is associated with a second scan lens and an aperture.

The third direction may be counterclockwise. The collection module may include detection unit optics and a rotating polygon mirror that may be configured to rotate in a clockwise direction in synchronicity with the counterclockwise propagation of the set of collected beams and to reflect, during multiple points in time, and towards the detection unit optics the set of output beams.

The third direction may be clockwise. The collection module may include detection unit optics and a rotating polygon mirror that may be configured to rotate in a counterclockwise direction in synchronicity with the clockwise propagation of the set of collected beams and to reflect, during multiple points in time, and towards the detection unit optics the set of output beams.

According to an embodiment of the invention there may be provided a method for inspecting an object, the method may include generating, by a first traveling lens acousto-optic device, a traveling lens that propagates through an active region of the traveling lens acousto-optic device; illuminating, by an illumination unit, the traveling lens to provide an input beam that propagates along a first direction; converting the input beam an output beam that scans the object at a second direction; collecting a collected beam from the object, the collected beam propagates along a third direction; optically manipulating the collected beam to provide a counter-scan beam that is directed towards the detection unit and has a focal point that is positioned at a same location regardless of the propagation of the collected beam along the third direction; and detecting the counter-scan beam by the detection unit.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2 illustrates beams and masking units according to various embodiments of the invention;

FIG. 8 illustrates a step of a method according to an embodiment of the invention.

Figure 1:
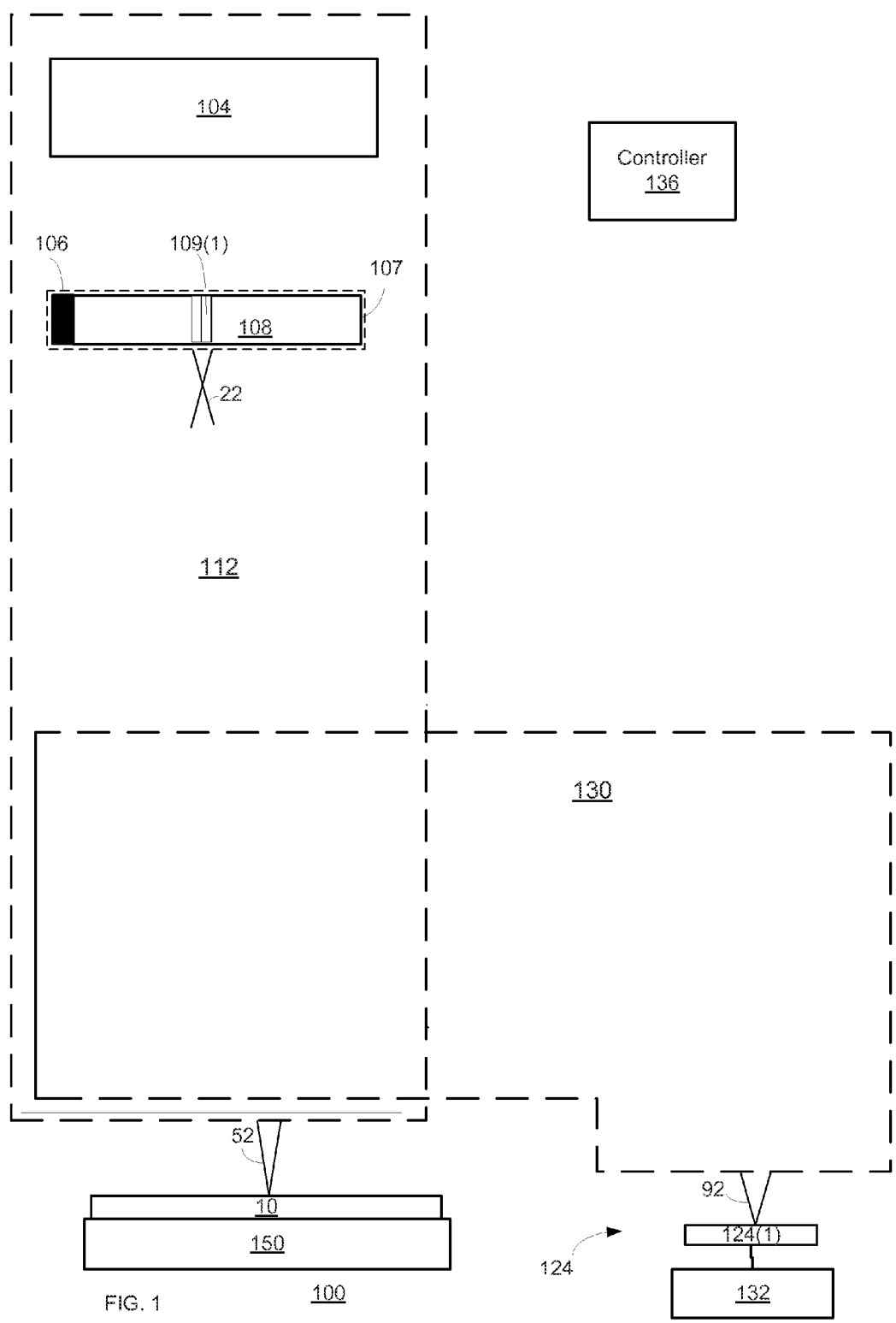
FIG. 1 illustrates a system and an object according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a subject surface by detecting reflected light using a light source and detecting unit that are disposed on a common side of an object (a "reflective system"), it would be readily apparent to one skilled in the art that the teachings are readily adaptable to the inspection of an object by detecting transmitted light with a detecting unit that is on a side of an object opposite to that of the light source (a "transmissive system").

While the reflective system and the transmissive system differ, for one example by the absence of a beam splitter in the transmissive system, the principles of the present invention are applicable to both types of systems. As would be understood by one skilled in the art, both types of systems may be utilized separately or together in the inspection of an object, in accordance with the present invention.

FIG. 1 illustrates system 100 and object 10 according to an embodiment of the invention.

Without limitation and only by example, object 10 may be any semiconductor product having multiple semiconductor devices thereon, at any of several steps of manufacture, or may be a mask, reticule or the like used in a manufacturing process, where such object must be inspected for defects, foreign objects or pattern accuracy. It is desirable in such systems to identify with high accuracy and reliability the size, location and type of structure, defect or object that appears on the object surface. It also is desirable to undertake such identification at high speed, in order to minimize the delay in the manufacturing process that is provided to the inspection and quality assurance steps.

System 100 is illustrated as including an illumination module 110, collection module 130, detection unit 124 that includes detector 124(1), image processor 132, mechanical stage 150 and controller 136.

Illumination module 110 includes first traveling lens acousto-optic device 107, light source 104 and illumination optics 112.

First traveling lens acousto-optic device 107 is configured to generate a first traveling lens 109(1) that propagates through an active region of the first traveling lens acousto-optic device.

The traveling lens acousto-optic device 107 can resemble the traveling lens of acousto-optic device illustrated in U.S. Pat. Nos. 6,809,808, 7,053,395, 6,943,898, 6,853,475, 7,528,940, and 7,002,695—all being incorporated herein by reference.

The Bragg cell 108 may include a single crystal that is effective to generate one or more traveling lenses in response to one or more radio frequency chirps.

The single crystal in the device may be composed of a material that is compatible with a ultraviolet (UV) light source, preferably having an acousto-optic medium made of $Al3O2$, GaAs or $TeO.sub.2$ glass, although other known materials having UV compatibility, may be used. The crystal may have an anti-reflective coating on each major side that rated at less than 0.5% for both sides. The traveling lens acousto-optic device may operate in a longitudinal acoustic mode at a wavelength of 266 nm and at a center frequency of 200 MHz with a bandwidth of 130 MHz. RF power may be less than 3.0 watts. The active aperture of the device may be 1.0 mm "H" by 60 mm "L" in one exemplary embodiment.

First traveling lens acousto-optic device 107 includes transducer 106 and Bragg cell 108 that acts as the active region of the traveling lens acousto-optic device.

Light source 104 is configured to illuminate the first traveling lens to provide an input beam 22 that propagates along a first direction.

Illumination optics 112 is configured to receive the input beam and to output, in response to the input beam, an output beam 52 that scans the object at a second direction.

Collection module 130 is configured to (a) collect a collected beam from the object, wherein the collected beam propagates along a third direction; (b) optically manipulate the collected beam to provide a counter-scan beam is directed towards the detection unit and has a focal point that is positioned at a same location regardless of the propagation of the collected beam along the third direction.

The phrase "optically manipulate" may include using one or more optical components to change an optical parameter (such as an optical path) of an optical beam.

In FIG. 1 the collected beam overlaps with output beam 52 and the second direction equals the third direction. It is noted that the collected beam may be oriented to the output beam 52 and that the second direction may differ from the third direction.

The propagation of the collected beam along the third direction may cause the counter-scan beam 92 to changes its angle in relation to the detection unit 124 but does not change the location of the focal plane of the counter-scan beam. In other words—the position of the counter-scan beam 92 on the detector remains the same.

It is noted that although FIG. 1 illustrates a single input beam, a single output beam and a single counter-scan beam, system 100 may be configured to generate a set of input beams, a set of output beams and a set of counter-scan beams. Each set may include two or more beams. Using a set of multiple output beams increases the throughput of system 100.

Figure 2:
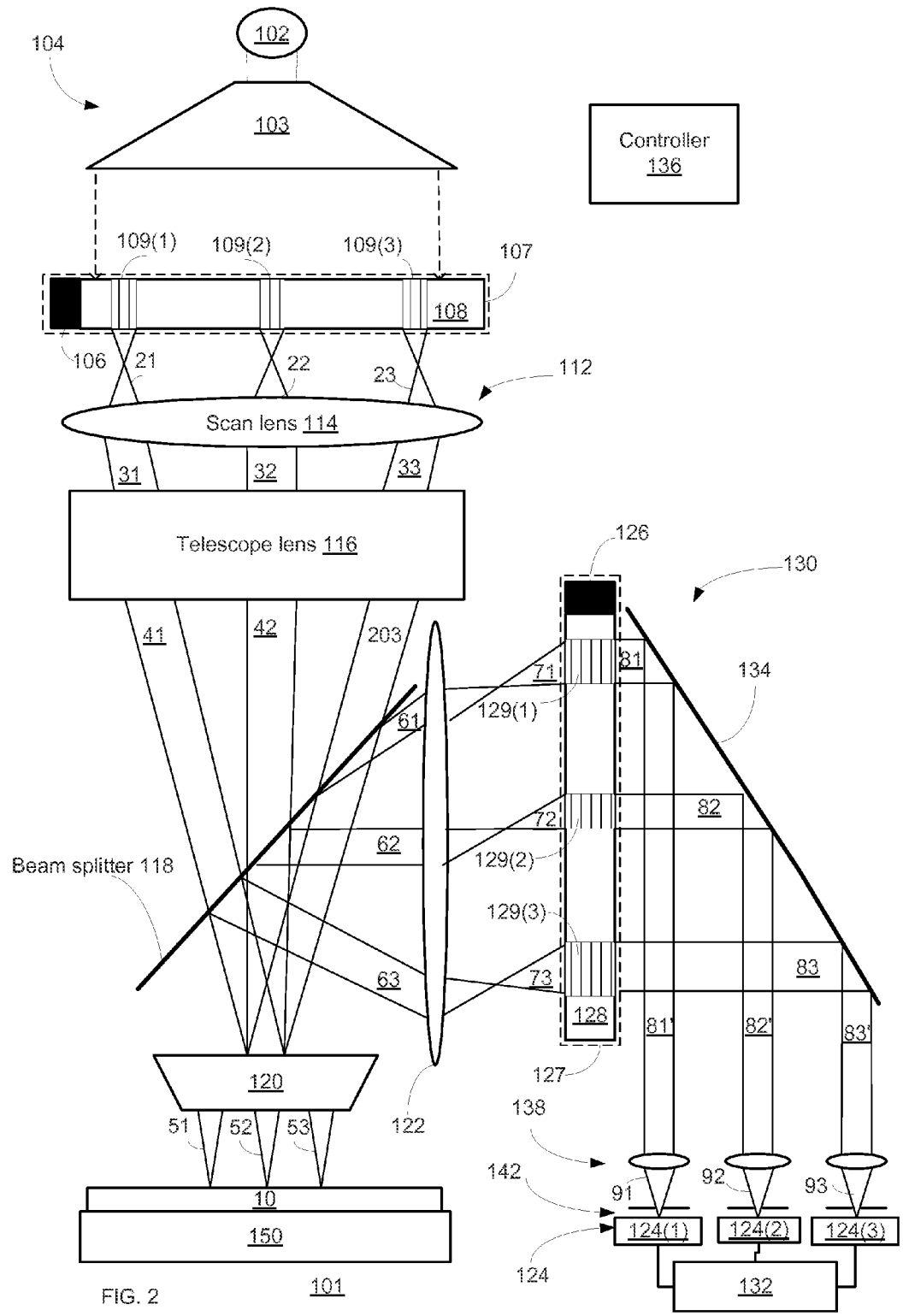
FIG. 2 illustrates a system and an object according to an embodiment of the invention.

FIG. 2 illustrates system 101 and object 10 according to an embodiment of the invention.

System 101 is illustrated as including an illumination module 110, collection module 130, detection unit 124, image processor 132 and controller 136.

Illumination module 110 includes first traveling lens acousto-optic device 107, light source 104 and illumination optics 112.

Light source 104 includes laser 102 and beam expander 103. Laser 102 may be replaced by another radiation source.

Illumination optics 112 includes scan lens 114 that is followed by telescope lens 116. Telescope lens 116 is followed by beam splitter 118. Beam splitter 118 is followed by objective lens 120.

Collection module 130 includes objective lens 120, beam splitter 118, tube lens 122, second traveling lens acousto-optic device 127, mirror 134, a set of second scan lenses 138, a set of apertures 142 and a detection unit 124 that includes a set of detectors that includes detectors 124(1), 124(2) and 124(3).

Second traveling lens acousto-optic device 127 includes transducer 126 and Bragg cell 128 that acts as the active region of the traveling lens acousto-optic device.

Second traveling lens acousto-optic device 127 is configured to generate a set of second traveling lenses 129(1), 129(2) and 129(3) that propagate through an active region of the second traveling lens acousto-optic device.

A set of input beams includes input beams 21, 22 and 23 that exit from first traveling lens acousto-optic device 107 and impinge on scan lens 114.

Scan lens 114 outputs a set of first intermediate beams includes first intermediate beams 31, 32 and 33 that impinge on telescope lens 116.

Telescope lens 116 outputs a set of second intermediate beams that includes second intermediate beams 41, 42 and 43 that pass through beam splitter 118 and impinge on objective lens 120.

Objective lens 120 outputs a set of output beams that includes output beams 51, 52 and 53 that may scan the object 10.

Objective lens 120 collects a set of collected beams (in FIG. 2 the set of output beams overlap output beams) that include collected beams that impinge on beam splitter 118 and are directed as a set of third intermediate beams on tube lens 122. The set of third intermediate beams includes third intermediate beams 61, 62 and 63.

Tube lens 122 outputs a set of fourth intermediate beams that includes fourth intermediate beams 71, 72 and 73 that illuminate the set of second traveling lenses to provide a set of fifth intermediate beams that includes fifth intermediate beams 81, 82 and 83.

Fifth intermediate beams 81, 82 and 83 impinge on mirror 134 that outputs a set of sixth intermediate beams that includes sixth intermediate beams 81', 82' and 83'. The orientation of sixth intermediate beams 81', 82' and 83' does not change.

Sixth intermediate beams 81', 82' and 83' impinge on the set of second scan lenses 138.

The set of second scan lenses 138 outputs a set of counter-scan beams that include counter-scan beams 91, 92 and 92 onto detection unit 124.

Figure 3:
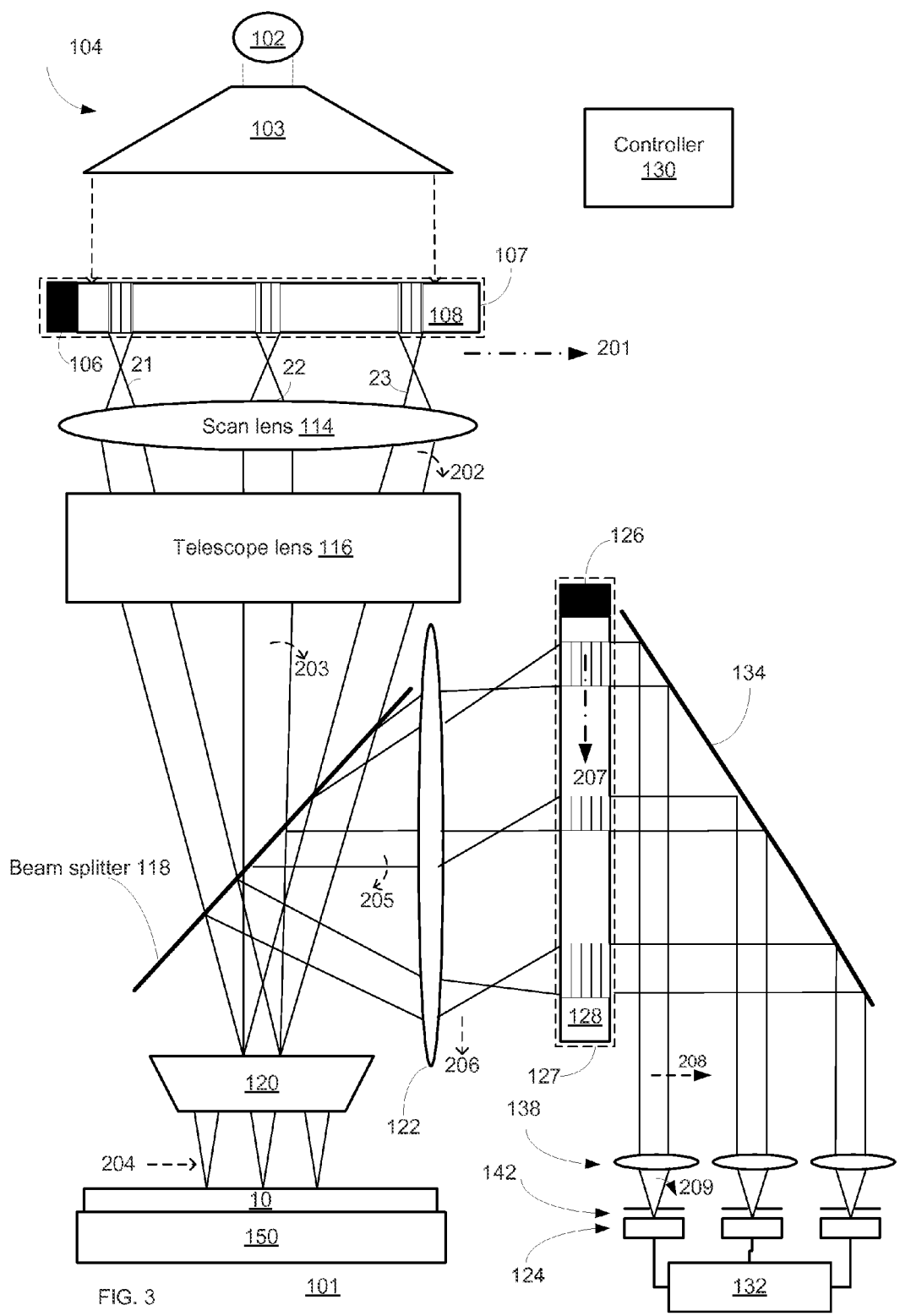
FIG. 3 illustrates a system and an object according to an embodiment of the invention.

FIG. 3 illustrates system 101, object 10 and propagation directions of various beams and traveling lenses according to an embodiment of the invention.

Various sets of beams propagate from optical component of the system 101 to the other. FIG. 3 illustrates the changes in the paths of the sets of beam over time—due to the propagation of the set of first traveling lenses within first traveling lens acousto-optic device 107.

In FIG. 3 it is assumed that first traveling lenses 109(1), 109(2) and 109(3) and input beams 21, 22 and 23 propagate along a first direction 201—to the right.

First intermediate beams 31, 32 and 33 of the set of first intermediate beams rotate clockwise 202.

Second intermediate beams 41, 42 and 43 of the set of second intermediate beams rotate clockwise 203.

Output beams 51, 52 and 52 and collected beams (overlap output beams 51, 52 and 53) propagate along second direction 204—to the right.

Third intermediate beams 61, 62 and 63 rotate clockwise 205.

Fourth intermediate beams 71, 72 and 73 propagate along a fourth direction 206—downwards.

Set of second traveling lenses 129(1), 129(2) and 129(3) propagate downwards 207.

Fifth intermediate beams 81, 82 and 83 propagate along a fifth direction 208- to the right.

Counter-scan beams 91, 92 and 92 rotate clockwise 209 but the focal point of counter-scan beams 91, 92 and 93 does not move.

Figure 4:
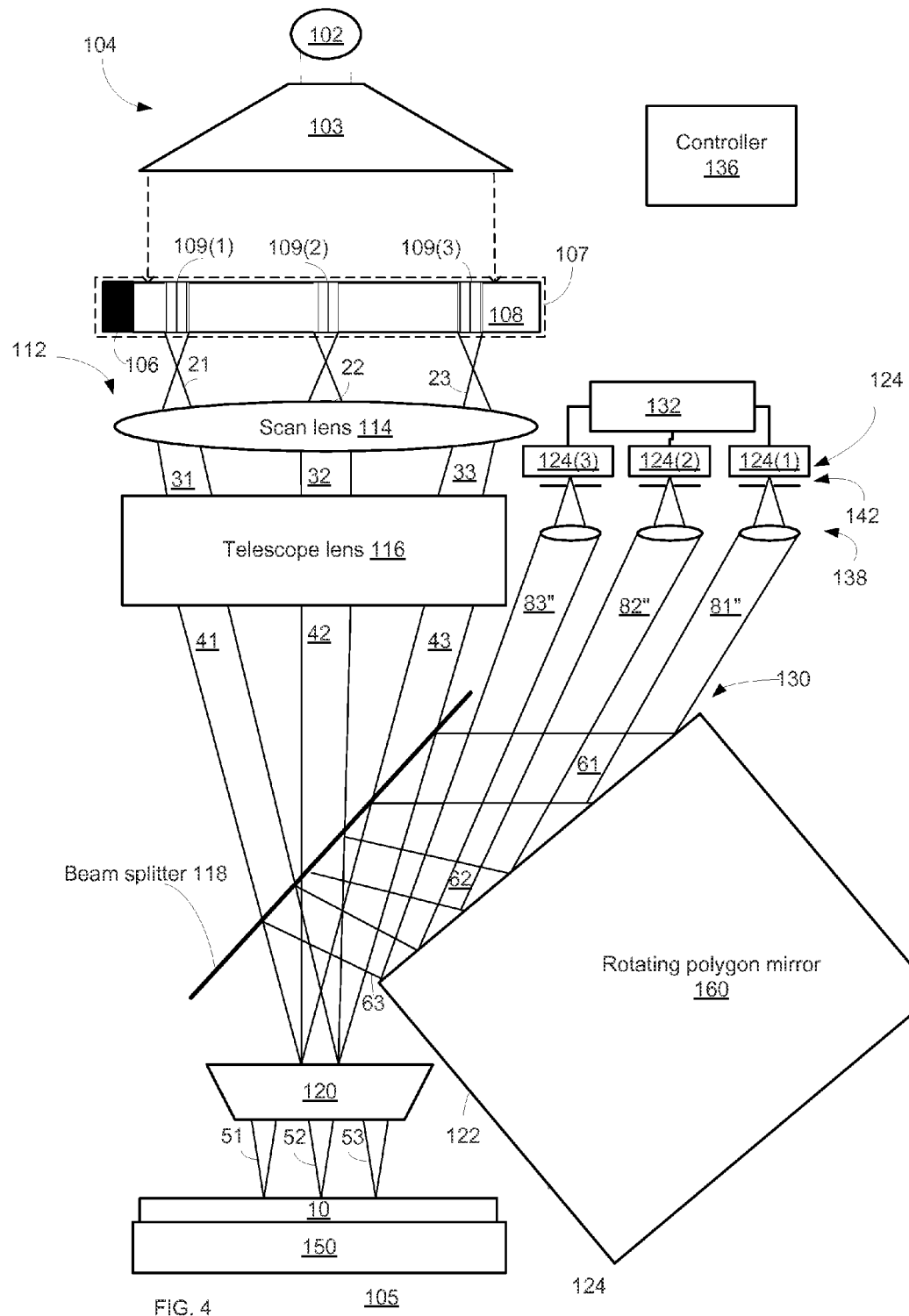
FIG. 4 illustrates a system and an object according to an embodiment of the invention.

FIG. 4 illustrates system 105 and object 10 according to an embodiment of the invention.

System 105 is illustrated as including an illumination module 110, collection module 130, detection unit 124, image processor 132 and controller 136.

Illumination module 110 includes first traveling lens acousto-optic device 107, light source 104 and illumination optics 112.

Light source 104 includes laser 102 and beam expander 103. Laser 102 may be replaced by another radiation source.

Illumination optics 112 includes scan lens 114 that is followed by telescope lens 116. Telescope lens 116 is followed by beam splitter 118. Beam splitter 118 is followed by objective lens 120.

Collection module 130 includes objective lens 120, beam splitter 118, rotating polygon mirror 160, a set of second scan lenses 138, a set of apertures 142 and a detection unit 124 that includes a set of detectors that includes detectors 124(1), 124(2) and 124(3).

A set of input beams includes input beams 21, 22 and 23 that exit from first traveling lens acousto-optic device 107 and impinge on scan lens 114.

Scan lens 114 outputs a set of first intermediate beams includes first intermediate beams 31, 32 and 33 that impinge on telescope lens 116.

Telescope lens 116 outputs a set of second intermediate beams that includes second intermediate beams 41, 42 and 43 that pass through beam splitter 118 and impinge on objective lens 120.

Objective lens 120 outputs a set of output beams that includes output beams 51, 52 and 53 that may scan the object 10.

Objective lens 120 collects a set of collected beams (in FIG. 2 the set of output beams overlap output beams) that include collected beams that impinge on beam splitter 118 and are directed as a set of third intermediate beams that includes third intermediate beams 61, 62 and 62 onto rotating polygon mirror 160.

The third intermediate beams 61, 62 and 63 rotate clockwise as a result of the propagation of the set of first traveling lenses within first traveling lens acousto-optic device 107.

Rotating polygon mirror 160 (especially the facets of the rotating polygon mirror) rotates in an opposite direction (for example counterclockwise) to the direction of rotation of third intermediate beams 61, 62 and 63 and in synchronization with the rotation of third intermediate beams 61, 62 and 63—thereby countering the rotation of third intermediate beams 61, 62 and 63.

The rotating polygon mirror 160 (especially the facets of the rotating polygon mirror) reflects towards the set of second scan lenses 138 a set of rotating polygon mirror output beams that includes rotating polygon mirror output beams 81", 82" and 83".

When the facets of the rotating polygon mirror 160 reflect the third intermediate beams 61, 62 and 63—the rotating polygon mirror output beams 81", 82" and 83" are stationary.

The system 105 may ignore the rotating polygon mirror output beams 81", 82" and 83" that are reflected by the edges of the rotating polygon mirror 160.

The rotating polygon mirror 160 is illustrates as including four facets. It is noted that the rotating polygon mirror 160 may include more facets than four. For example—the rotating polygon mirror 160 may have 20 facets, 30 facets and even more. An increase in the number of facets of the rotating polygon mirror 160 increases the stability of the rotating polygon mirror output beams 81", 82" and 83".

The set of second scan lenses 138 outputs a set of counter-scan beams that includes counter-scan beams 91, 92 and 92 onto the detection unit 124.

Figure 5:
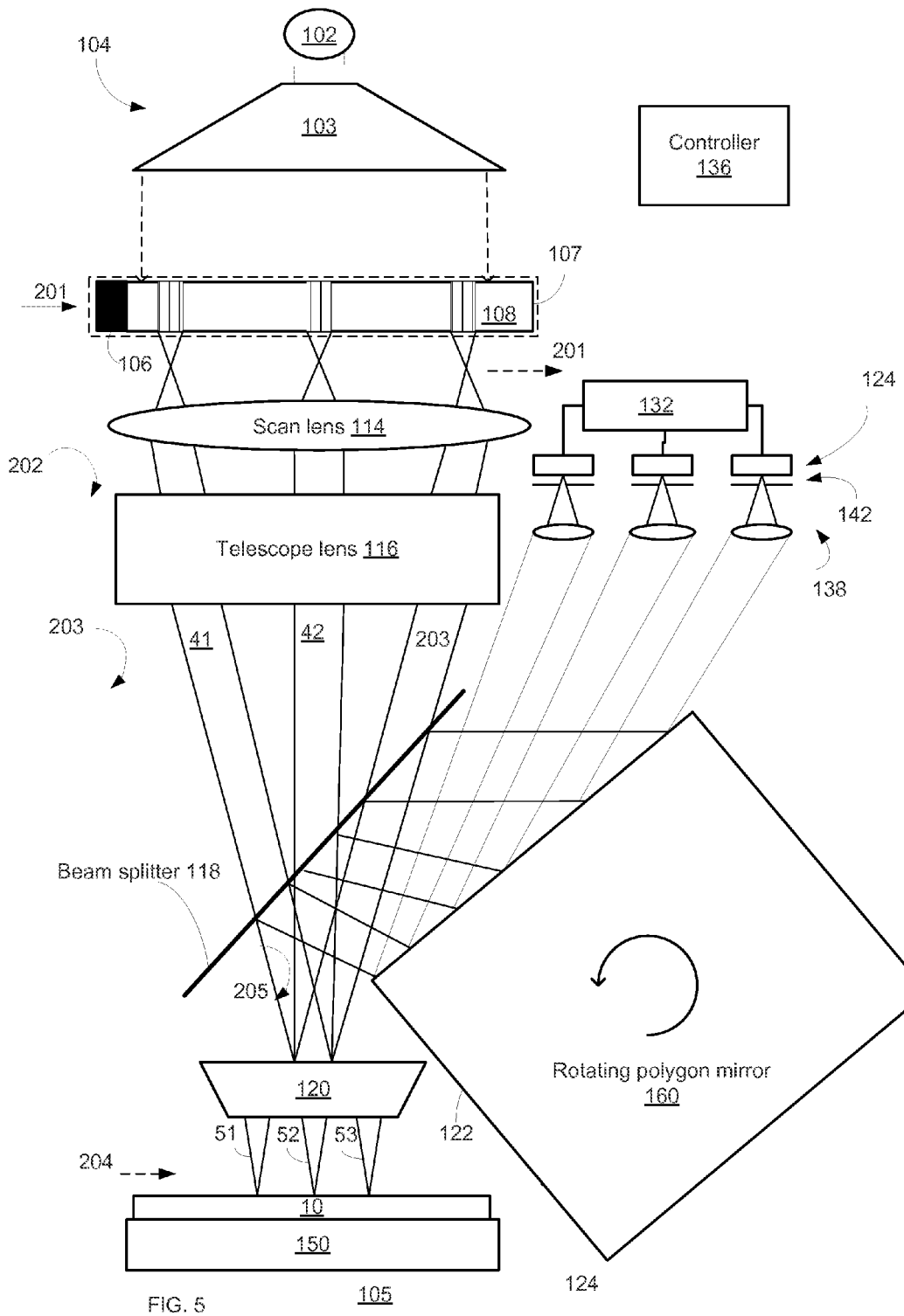
FIG. 5 illustrates a system and an object according to an embodiment of the invention.

FIG. 5 illustrates system 105, object 10 and propagation directions of various beams and traveling lenses according to an embodiment of the invention.

Various sets of beams propagate from optical component of the system 101 to the other. FIG. 5 illustrates the changes in the paths of the sets of beam over time—due to the propagation of the set of first traveling lenses within first traveling lens acousto-optic device 107.

In FIG. 5 it is assumed that first traveling lenses 109(1), 109(2) and 109(3) and input beams 21, 22 and 23 propagate along a first direction 201—to the right.

First intermediate beams 31, 32 and 33 of the set of first intermediate beams rotate clockwise 202.

Second intermediate beams 41, 42 and 43 of the set of second intermediate beams rotate clockwise 203.

Output beams 51, 52 and 52 and collected beams (overlap output beams 51, 52 and 53) propagate along second direction 204—to the right.

Third intermediate beams 61, 62 and 63 rotate clockwise 205.

Rotating polygon mirror output beams 81", 82" and 83" are static (when reflected by the facets of the rotating polygon mirror 160).

Counter-scan beams 91, 92 and 92 are static.

Figure 6:
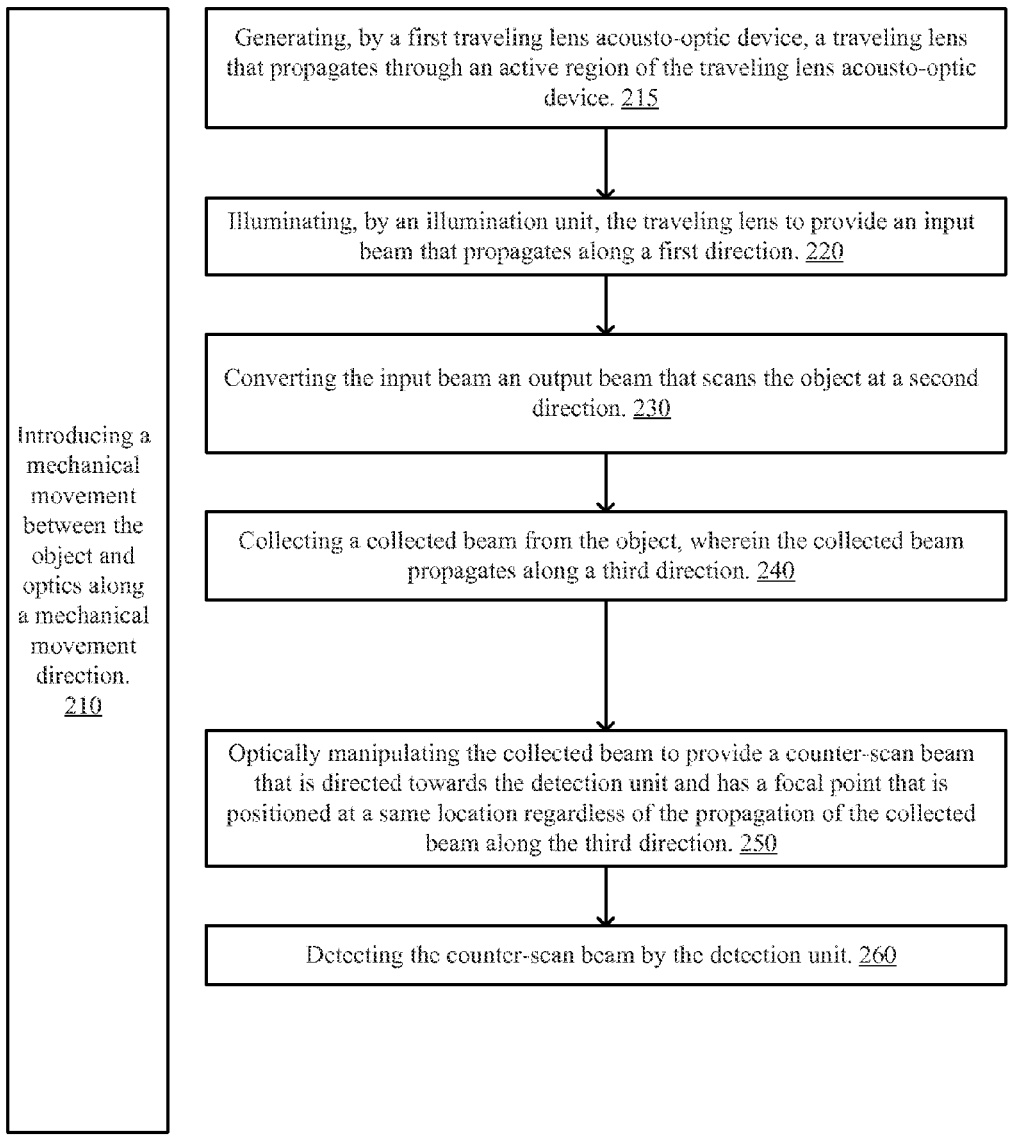
FIG. 6 illustrates a method according to an embodiment of the invention.

FIG. 6 is a flow chart illustrating method 200 for inspecting an object according to an embodiment of the present invention.

Method 200 may be executed by system 100 of FIG. 1, system 101 of FIG. 2 and system 105 of FIG. 4.

It is noted that various steps of method 200 at least partially overlap and that their order as illustrated in FIG. 6 is not mandatory.

Method 200 may start by steps 210 and 215.

Step 210 may include introducing a mechanical movement between the object and optics along a mechanical movement direction. Step 210 may be executed in parallel to steps 215, 220, 230, 240, 250 and 260.

Step 215 may include generating, by a first traveling lens acousto-optic device, a traveling lens that propagates through an active region of the traveling lens acousto-optic device.

Step 215 may be followed by step 220 of illuminating, by an illumination unit, the traveling lens to provide an input beam that propagates along a first direction.

Step 220 may be followed by step 230 of converting the input beam an output beam that scans the object at a second direction. The second direction may be oriented to the mechanical movement direction or may be parallel to the mechanical movement direction.

Step 230 may be followed by step 240 of collecting a collected beam from the object, wherein the collected beam propagates along a third direction.

Step 240 may be followed by step 250 of optically manipulating the collected beam to provide a counter-scan beam that is directed towards the detection unit and has a focal point that is positioned at a same location regardless of the propagation of the collected beam along the third direction.

Step 250 may be followed by step 260 of detecting the counter-scan beam by the detection unit.

Figure 7:
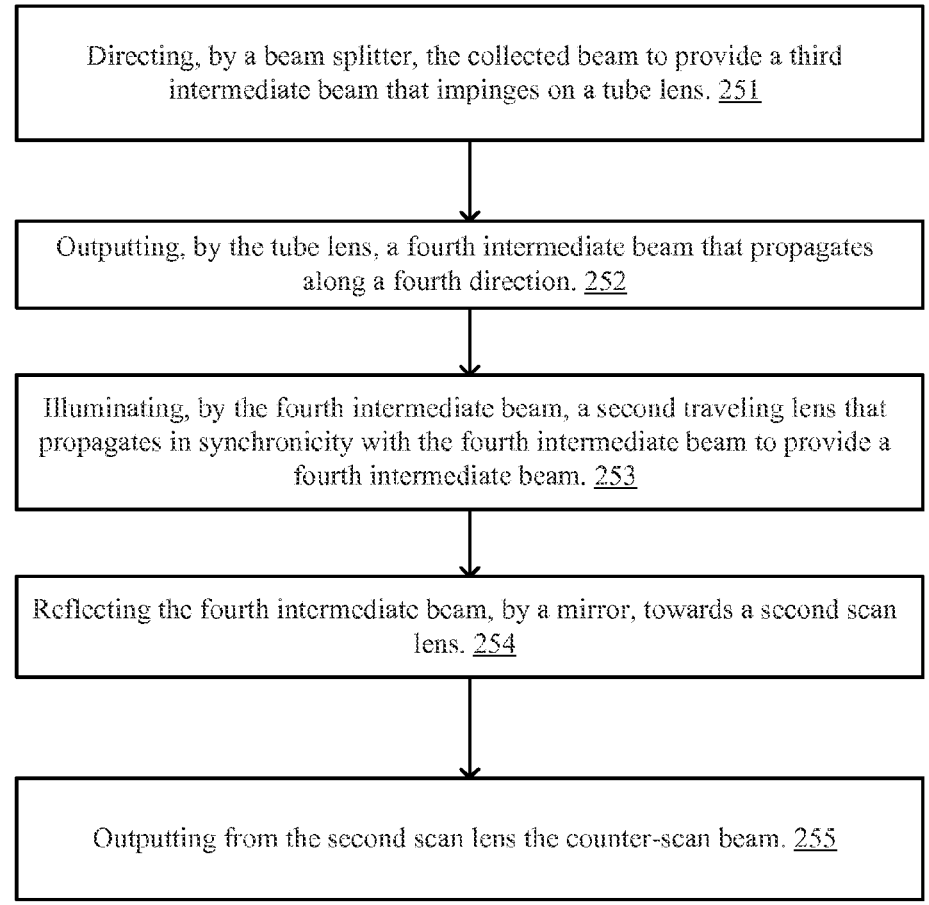
FIG. 7 illustrates a step of a method according to an embodiment of the invention.

FIG. 7 illustrates step 250 of method 200 according to an embodiment of the invention.

Step 250 may include a sequence of steps 251, 252, 252, 254 and 255.

Step 251 may include directing, by a beam splitter, the collected beam to provide a third intermediate beam that impinges on a tube lens.

Step 252 may include outputting, by the tube lens, a fourth intermediate beam that propagates along a fourth direction.

Step 253 may include illuminating, by the fourth intermediate beam, a second traveling lens that propagates in synchronicity with the fourth intermediate beam to provide a fourth intermediate beam.

Step 254 may include reflecting the fourth intermediate beam, by a mirror, towards a second scan lens.

Step 255 may include outputting from the second scan lens the counter-scan beam.

FIG. 8 illustrates step 250 of method 200 according to an embodiment of the invention.

Step 250 may include a sequence of steps 256, 257 and 258.

Step 256 may include directing, by a beam splitter, the collected beam to provide a third intermediate beam that impinges on a rotating polygon mirror. While the third intermediate rotates along a first rotation direction the rotating polygon mirror rotates at a same rotational rate but along an opposite rotation direction thereby countering the rotation of the third intermediate beam.

For example—when the first rotation direction is clockwise the second rotation direction is counterclockwise. Yet for another example—when the first rotation direction is counterclockwise the second rotation direction is clockwise Step 257 may include reflecting, by facets of the rotating polygon mirror, the third intermediate beam to provide a rotating polygon mirror output beam that is static when reflected by the facets of rotating polygon mirror.

Step 258 includes outputting from the second scan lens the counter-scan beam.

Figure 9:
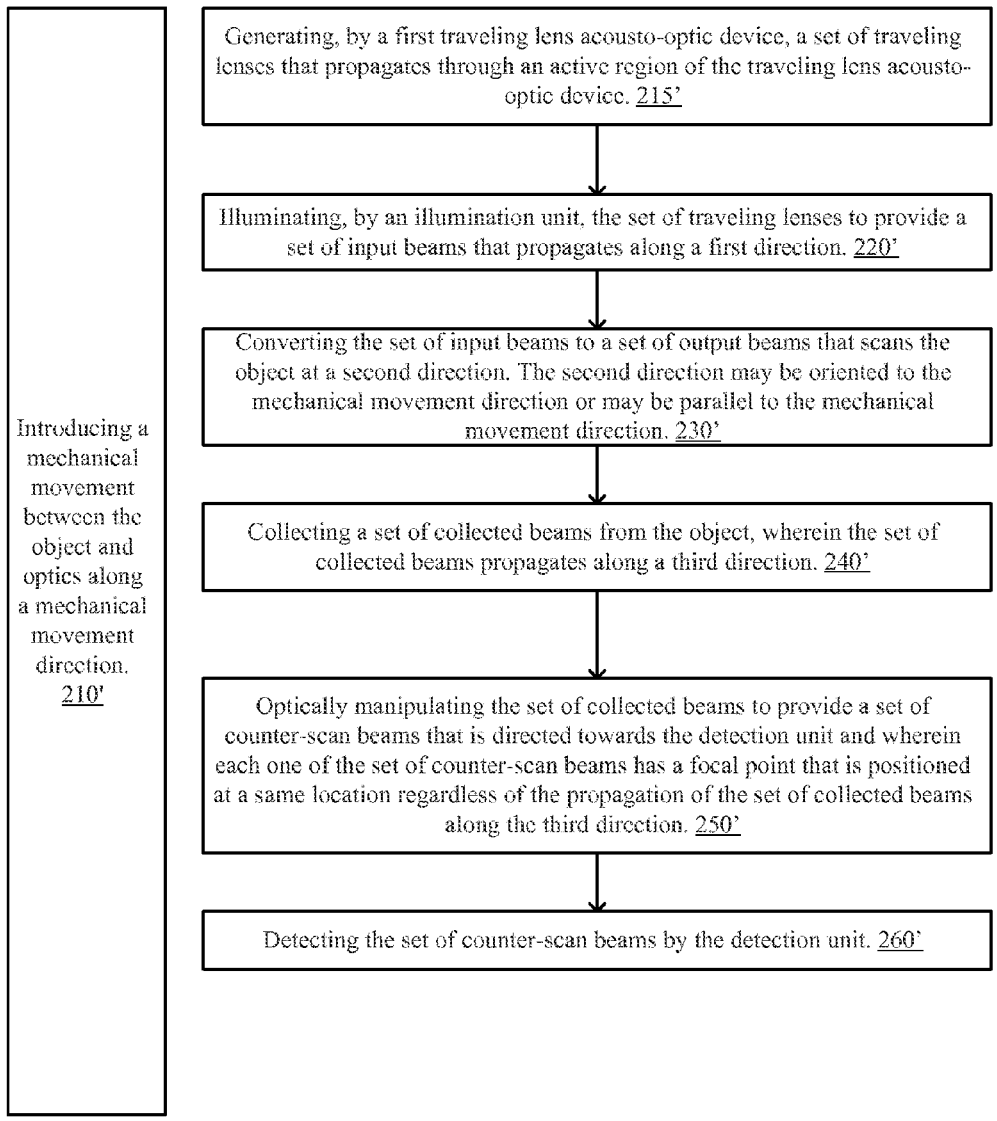
FIG. 9 illustrates a method according to an embodiment of the invention.

FIG. 9 is a flow chart illustrating method 200' for inspecting an object according to an embodiment of the present invention.

Method 200' may be executed by system 100 of FIG. 1, system 101 of FIG. 2 and system 105 of FIG. 4.

It is noted that various steps of method 200 at least partially overlap and that their order as illustrated in FIG. 9 is not mandatory.

Method 200' may start by steps 210' and 215'.

Step 210' may include introducing a mechanical movement between the object and optics along a mechanical movement direction. Step 210' may be executed in parallel to steps 215', 220', 230', 240', 250' and 260.

Step 215' may include generating, by a first traveling lens acousto-optic device, a set of traveling lenses that propagates through an active region of the traveling lens acousto-optic device.

Step 215' may be followed by step 220' of illuminating, by an illumination unit, the set of traveling lenses to provide a set of input beams that propagates along a first direction.

Step 220' may be followed by step 230' of converting the set of input beams to a set of output beams that scans the object at a second direction. The second direction may be oriented to the mechanical movement direction or may be parallel to the mechanical movement direction.

Step 230' may be followed by step 240' of collecting a set of collected beams from the object, wherein the set of collected beams propagates along a third direction.

Step 240' may be followed by step 250' of optically manipulating the set of collected beams to provide a set of counter-scan beams that is directed towards the detection unit and wherein each one of the set of counter-scan beams has a focal point that is positioned at a same location regardless of the propagation of the set of collected beams along the third direction.

Step 250' may be followed by step 260' of detecting the set of counter-scan beams by the detection unit.

In method 200 and method 200' the detection of the set of counter scan beams may be followed by generating detection signals by the detection unit and executing at least one step out of storing the detection signals, processing the detection signals to provide an inspection result and transmitting the detection signals.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A system for inspecting an object, the system comprising:
   an illumination module that comprises (a) a first traveling lens acousto-optic device that is configured to generate a first traveling lens that propagates through an active region of the first traveling lens acousto-optic device; (b) a light source that is configured to illuminate the first traveling lens to provide an input beam that propagates along a first direction; (c) illumination optics that are configured to receive the input beam and to output, in response to the input beam, an output beam that scans the object along a second direction;
   a detection unit; and
   a collection module that is configured to (a) collect a collected beam from the object, wherein the collected beam propagates along a third direction; and (b) optically manipulate the collected beam to provide a counter-scan beam that is directed towards the detection unit and has a focal point that is positioned at a same location regardless of the propagation of the collected beam along the third direction.

2. The system according to claim 1 wherein the collection module is configured to counter-scan the collected beam to provide the counter-scan beam.

3. The system according to claim 1 wherein the collection module comprises a second traveling lens acousto-optic device that is configured to generate a second traveling lens that propagates through an active region of the second traveling lens acousto-optic device along a fourth direction.

4. The system according to claim 3 wherein the illumination module comprises a first scan lens and the collection module comprises a mirror, a second scan lens and an aperture; and wherein the mirror, the second scan lens and the aperture are positioned between the second traveling lens acousto-optic device and the detection unit.

5. The system according to claim 4 wherein the traveling lens propagates through the active region in synchronization with the propagation of the collected beam along the third direction.

6. The system according to claim 5 wherein an output beam of the second traveling lens acousto-optic device impinges on the mirror and is directed by the mirror towards the second scan lens to provide a mirror output beam that propagates along a fifth direction while maintaining a fixed angle in relation to the second scan lens; and wherein the second scan lens is configured to receive the mirror output beam to provide the counter-scan beam.

7. The system according to claim 6 wherein the illumination module comprises a telescope lens, a beam splitter and an objective lens; wherein the collection module comprises the beam splitter, the objective lens and a tube lens; wherein the telescope lens is positioned between the beam splitter and the first scan lens; and wherein the tube lens is positioned between the beam splitter and the second traveling lens acousto-optic device.

8. The system according to claim 1, wherein the collection module optically manipulates the collected beam to provide an intermediate beam that rotates counterclockwise; and wherein the collection module comprises detection unit optics and a rotating polygon mirror that is configured to rotate in a clockwise direction in synchronicity with the counterclockwise rotation of the intermediate beam and to reflect, during multiple points in time, towards the detection unit optics the output beam.

9. The system according 8 wherein the illumination module comprises a first scan lens, a telescope lens, a beam splitter and an objective lens; wherein the collection module comprises the beam splitter, the objective lens, a second scan lens and an aperture; and wherein the beam splitter directs the intermediate beam towards the rotating polygon mirror.

10. The system according to claim 1, wherein the collection module optically manipulates the collected beam to provide an intermediate beam that rotates counterclockwise; and wherein the collection module comprises detection unit optics and a rotating polygon mirror that is configured to rotate in a clockwise direction in synchronicity with the counterclockwise rotation of the intermediate beam and to reflect, during multiple points in time, towards the detection unit optics the output beam.

11. The system according 10 wherein the illumination module comprises a first scan lens, a telescope lens, a beam splitter and an objective lens; wherein the collection module comprises the beam splitter, the objective lens, a second scan lens and an aperture; and wherein the beam splitter directs the intermediate beam towards the rotating polygon mirror.

12. The system according to claim 1, wherein the first traveling lens acousto-optic device is configured to generate a set of first traveling lenses that propagates through the active region of the first traveling lens acousto-optic device; wherein the light source is configured to illuminate the set of first traveling lenses to provide a set of input beams that propagates along the first direction; wherein the illumination optics are configured to receive the set of input beams and to output, in response to the set of input beams, a set of output beams that scans the object along the second direction; wherein the collection module is configured to (a) collect a set of collected beams from the object, wherein the set of collected beams propagates along a third direction; and (b) optically manipulate the collected beams to provide a set of counter-scan beams that is directed towards the detection unit; and wherein each counter-scan beam of the set of counter-scan beams has a focal point that is positioned at a same location regardless of the propagation of the set of collected beams along the third direction.

13. The system according to claim 12 wherein the collection module comprises a second traveling lens acousto-optic device that is configured to generate a set of second traveling lenses that propagates through the active region of the second traveling lens acousto-optic device along the fourth direction.

14. The system according to claim 12, wherein the third direction is clockwise; wherein the collection module comprises detection unit optics and a rotating polygon mirror that is configured to rotate in a counterclockwise direction in synchronicity with the clockwise propagation of the set of collected beams and to reflect, during multiple points in time, towards the detection unit optics the set of output beams.

15. A method for inspecting an object, the method comprises:

generating, by a first traveling lens acousto-optic device, a traveling lens that propagates through an active region of the traveling lens acousto-optic device;

illuminating, by an illumination unit, the traveling lens to provide an input beam that propagates along a first direction;

converting the input beam into an output beam that scans the object at a second direction;

collecting a collected beam from the object, wherein the collected beam propagates along a third direction;

optically manipulating the collected beam to provide a counter-scan beam that is directed towards the detection unit and has a focal point that is positioned at a same location regardless of the propagation of the collected beam along the third direction; and detecting the counter-scan beam by the detection unit.

* * * * *